United States Patent
He

(10) Patent No.: US 11,939,475 B2
(45) Date of Patent: Mar. 26, 2024

(54) METHOD FOR CHLORINATING BLUE ANTHRONE, VIOLANTHRONE OR ISOVIOLANTRONE

(71) Applicant: Xiaohan He, Jiangsu (CN)

(72) Inventor: Xiaohan He, Jiangsu (CN)

( * ) Notice: Subject to any disclaimer, the term of this patent is extended or adjusted under 35 U.S.C. 154(b) by 143 days.

(21) Appl. No.: 17/630,532

(22) PCT Filed: Jul. 12, 2021

(86) PCT No.: PCT/CN2021/105751
§ 371 (c)(1),
(2) Date: Jan. 27, 2022

(87) PCT Pub. No.: WO2022/147994
PCT Pub. Date: Jul. 14, 2022

(65) Prior Publication Data
US 2023/0159761 A1 May 25, 2023

(30) Foreign Application Priority Data
Jan. 6, 2021 (CN) .................. 202110013918.X

(51) Int. Cl.
| C07C 45/63 | (2006.01) |
| C07D 311/36 | (2006.01) |
| C09B 3/32 | (2006.01) |
| C09B 6/00 | (2006.01) |
| C09B 67/14 | (2006.01) |

(52) U.S. Cl.
CPC ............. *C09B 3/32* (2013.01); *C07C 45/63* (2013.01); *C07D 311/36* (2013.01); *C09B 6/00* (2013.01); *C09B 67/0017* (2013.01); *C07C 2603/24* (2017.05); *C07C 2603/54* (2017.05)

(58) Field of Classification Search
CPC .. C07C 45/63; C07C 2603/24; C07C 2603/54
See application file for complete search history.

(56) References Cited

FOREIGN PATENT DOCUMENTS

| CN | 1111663 | 11/1995 |
| CN | 1071777 | 9/2001 |
| CN | 1865355 | 11/2006 |
| CN | 101270110 | 9/2008 |
| CN | 104892426 | 9/2015 |
| CN | 107974099 | 5/2018 |
| CN | 108047017 | 5/2018 |
| CN | 111087833 | 5/2020 |
| CN | 111087833 A * | 5/2020 |
| CN | 112778789 | 5/2021 |
| JP | 863291959 | 11/1988 |
| WO | WO-02072260 A2 * | 9/2002 .......... B01J 31/0222 |

OTHER PUBLICATIONS

"International Search Report (Form PCT/ISA/210) of PCT/CN2021/105751," dated Sep. 27, 2021, pp. 1-5.
"Written Opinion of the International Searching Authority (Form PCT/ISA/237) of PCT/ CN2021/105751," dated Sep. 27, 2021, pp. 1-4.

* cited by examiner

*Primary Examiner* — Amanda L. Aguirre
(74) *Attorney, Agent, or Firm* — JCIP GLOBAL INC.

(57) ABSTRACT

A method for chlorinating blue anthrone, violanthrone or isoviolantrone is provided. Reaction is carried out with a chlorinating agent (any one of sulfonyl chloride, thionyl chloride and triphosgene) in a reaction solvent (a Lewis acid ionic liquid with anions being of a transition metal halide) for 2 h to 40 h at a chlorination temperature not lower than room temperature and not higher than 120° C.; and then the reaction product is subjected to post-treatment to obtain a target product. The present disclosure cuts off a generation route of harmful substances such as dioxins and their derivatives from the source. There are no dioxins or similar substances generated in the product, and the reaction has high atomic utilization rate and low energy consumption, which fills the gap in the field of chemical technologies at home and abroad.

15 Claims, 4 Drawing Sheets

METHOD FOR CHLORINATING BLUE ANTHRONE, VIOLANTHRONE OR ISOVIOLANTRONE

CROSS-REFERENCE TO RELATED APPLICATION

This application is a 371 of international application of PCT application serial no. PCT/CN2021/105751, filed on Jul. 12, 2021, which claims the priority benefit of China application no. 202110013918.X, filed on Jan. 6, 2021. The entirety of each of the above mentioned patent applications is hereby incorporated by reference herein and made a part of this specification.

BACKGROUND

Technical Field

The present disclosure relates to a method for chlorinating blue anthrone, violanthrone or isoviolanthrone, and belongs to the technical field of organic vat dyes.

Description of Related Art

In recent years, environmental pollution caused by various by-products in the chemical process has become more and more serious. Dioxins and their derivatives, quinoline and other highly toxic, difficult-to-degrade industrial by-products have caused serious harm to the environment and the human body, and have aroused widespread concern in the society. The halogenation process of blue anthrone, violanthrone and isoviolanthrone (hereinafter referred to as reaction substrates) is described here as an example. In the halogenation reaction of these substances, extremely dangerous and extremely toxic solvents such as chlorosulfonic acid, nitrobenzene, and chlorobenzene are often required for dissolving reaction substrates. On one hand, it is extremely harmful to the operators and the operation process is extremely dangerous. On the other hand, volatile organic pollutants VOC are emitted during the production process. In addition, in the prior art, oxidizing reagents such as bromine, chlorine gas, sodium hypochlorite, and sodium chlorate are often used as halogenating agents. Such halogenating agents will react with solvents at temperatures above 80° C., causing the contents of dioxins (strong carcinogenic products) and their derivatives in products to exceed the standard.

At present, the production of a halogenated product of violet anthrone or isoviol anthrone is carried out under the following process conditions: each gram of a reaction substrate is dissolved in 8 mL of a mixed solution of an aromatic hydrocarbon and its derivatives at a temperature of 150° C.; the resulting solution is then cooled to 80° C.; chlorine gas is introduced for 24 h or more; or, sodium hypochlorite is added dropwise as a chlorinating agent in a dosage 1.2 to 1.8 times the molar mass of the reaction substrate and then the resulting solution was held at the current temperature for 24 h.

A typical pilot test process is as follows:
step 1: dissolution: adding 200 g of nitrobenzene into a 250 ml three-necked flask, adding 20 g of isoviolanthrone with stirring, heating up to the boiling point (200° C. to 209° C.), and stirring for 1 h; step 2: chlorination; cooling down to 60° C., adding 34 g of sulfonyl chloride and 0.5 g of iodine, heating up to 70° C. to 75° C., holding the temperature and stirring for 24 h; wherein the temperature during the whole reaction should not be higher than 75° C.; and step 3: post-treatment: after completion of the reaction, cooling down to 60° C. and the filtering, washing with water and drying.

A typical industrial scale-up process is as follows:
step 1: dissolution: adding 2200 kg of sulfuric acid and 400 kg of dry blue anthrone powder in a 33 chlorination tank, and stirring for 2 h to dissolve the dry blue anthrone powder; cooling down to 50° C. or below, adding 20 kg of manganese dioxide, and stirring for 30 min; step 2: chlorination; introducing chlorine for about 20 h at 48° C. to 54° C., taking a sample to measure a chlorine content, stopping the chlorine when the chlorine content is qualified and reaches 10% to 13%, then cooling the reaction solution to 40° C., and discharging; and step 3: post-treatment; cooling and resting still, filtering, washing with water and drying.

The above processes usually generate dioxins and their derivatives, and the content of by-products in the products exceeds the standard.

The German BASF company's patent (CN1071777C) has improved the solvent by replacing the highly toxic solvents such as chlorosulfonic acid, nitrobenzene, and chlorobenzene with aliphatic carboxylic acid or halogenated carboxylic acid, such as acetic acid, and uses chlorine gas as a chlorinating agent to produce chlorinated violet anthrone or chlorinated isoviol anthrone. However, this solution essentially uses organic solvents, and in the preferred solutions, acetic acid or the like is more corrosive to equipment, additional catalysts are required during the reaction process, and the reaction temperature is relatively high. Therefore, although the use of nitrobenzene is avoided, the overall cost is relatively high. Compared with the solution using a liquid chlorinating agent, the solution using chlorine gas as a chlorinating agent is more dangerous in operation and production.

The halogenated products of blue anthrone, violanthrone and isoviolanthrone are all high value-added organic vat dyes with high economic value. However, as mentioned above, how to halogenate blue anthrone, violanthrone and isoviolanthrone more safely, environmentally and efficiently, and balance the relationship between economy and environment and between economy and public health is an important issue that needs to be resolved urgently.

The present disclosure mainly studies the chlorination process, is committed to finding new solvents, chlorinating agents and efficient production processes, and strives to obtain a plan that can jointly improve economic, social and environmental benefits.

SUMMARY

The present disclosure cuts off a generation route of harmful substances such as dioxins and their derivatives from the source during the chlorination of blue anthrone, violanthrone or isoviolanthrone by using a new solvent. There are no dioxins or similar substances generated in the product, and the reaction has high atomic utilization rate and low energy consumption, which fills the gap in the field of chemical technologies at home and abroad.

The technical solutions of the present disclosure are specifically as follows.

The present disclosure provides a method for chlorinating blue anthrone, violanthrone or isoviolanthrone, including: causing a reaction substrate (any one of blue anthrone, violanthrone and isoviolanthrone) to react with a chlorinating agent (any one of sulfonyl chloride, thionyl chloride and triphosgene) in a reaction solvent (a Lewis acid ionic liquid) for 2 h to 40 h at a chlorination temperature not lower than room temperature and not higher than a boiling point of the chlorinating agent; anions in the Lewis acid ionic liquid are of a transition metal halide.

Preferably, the anions in the Lewis acid ionic liquid are of any one of aluminum chloride and ferric chloride.

Preferably, a molar ratio of the anion to cation in the Lewis acid ionic liquid is (2.0 to 2.7):1.

Preferably, the cations in the Lewis acid ionic liquid are of any one of a tertiary amine hydrochloride (such as triethylamine hydrochloride and dimethylaniline hydrochloride), a tertiary amine sulfate (such as triethylamine sulfate and dimethylaniline sulfate), N-alkylpyridine, and urea.

Preferably, a mass concentration of the reaction substrate in the Lewis acid ionic liquid is 0.08 g/mL to 0.5 g/mL.

Preferably, for linking every 1 mol of chlorine atoms to the reaction substrate, 0.3 mol to 6 mol of the chlorinating agent needs to be added.

The present invention further provides a production process for chlorinating blue anthrone, violanthrone or isoviolanthrone, and the specific chlorination process includes the following steps:

step 1: dissolution; dissolving the reaction substrate in the Lewis acid ionic liquid at a dissolution temperature of 30° C. to 150° C., holding the dissolution temperature and stirring for not less than 3 h to obtain an initial reaction solution;

step 2: chlorination: adding the chlorinating agent dropwise to the initial reaction solution, wherein the temperature of the initial reaction solution is controlled to be not higher than 60° C. during the addition of the chlorinating agent; and then holding the chlorination temperature and stirring for 2 h to 40 h to obtain an end-point reaction solution; and step 3: post-treatment: hydrolyzing the end-point reaction solution for 10 min to 30 min, and then carrying out suction filtration, washing, and drying to obtain a target chlorination product.

Preferably, the chlorinating agent is added dropwise at a rate not greater than $1.35 \times 10^{-4}$ mol/[(L ionic liquid)·s].

Preferably, when the chlorinating agent is added dropwise, the temperature of the initial reaction liquid is controlled to be 40° C. to 50° C.

Preferably, when the reaction substrate is blue anthrone, the target chlorination product is dichloro-blue anthrone; when the reaction substrate is violanthrone, the target chlorination product is polychloroviolanthrone; when the reaction substrate is isoviolanthrone, the target chlorination product is dichloroisoviolanthrone.

The beneficial effects of the present disclosure are as follows.

In the art, the color of the dye is often expected to be brighter, and the higher the reflectivity, the better the color. The quantity of the product prepared by using the technical solution of the present disclosure, without using nitrobenzene, chlorobenzene and other highly toxic solvents, can reach the international advanced level, or even better, the obtained chlorides of violanthrone, blue anthrone and isoviolanthrone are brighter in color.

Specifically, during the chlorination of blue anthrone, violanthrone or isoviolanthrone in the present disclosure, the Lewis acid ionic liquid that is highly soluble, environmentally friendly, easy to recycle, and has catalytic properties is used as the reaction solvent, traditional organic solvents that are volatile, flammable and easy to by-produce harmful substances are not required. During the reaction, no high-toxic by-products such as dioxins and quinoline are produced, not to mention the situation where the contents of dioxins and their derivatives, as well as quinoline and other substances in the product exceed the standard. In addition, some solvents can be recycled and reused. Moreover, compared with use of chlorine gas or the like, the use of sulfonyl chloride, thionyl chloride or triphosgene as the chlorinating agent improves the utilization of atoms in the reaction and reduces the generation of undesired products. Furthermore, the ionic liquid solvent used in the present disclosure also has catalytic properties, which can effectively improve the efficiency of the reaction. In combination with the chlorinating agent, the reaction temperature during the entire chlorination process is also reduced, and no additional pressure is required, which significantly reduces energy consumption.

BRIEF DESCRIPTION OF THE DRAWINGS

The present disclosure will be further described with reference to the accompanying drawings.

In all the above reflectivity curves, the abscissa represents wavelength in nm and the ordinate represents the reflectivity in %.

DESCRIPTION OF THE EMBODIMENTS

Example 1

Step 0: preparation stage: 0.233 mol of triethylamine hydrochloride and 0.500 mol of aluminum chloride were put in a reaction kettle in sequence, and the resulting solution was then heated to 60° C. and then stirred for 40 min at this temperature to synthesize triethylamine hydrochloride-aluminum chloride ionic liquid.

Step 1: dissolution: 10 g of blue anthrone was dissolved into the triethylamine hydrochloride-aluminum chloride ionic liquid, and the resulting solution was heated to 80° C.

so that the blue anthrone was dissolved at this temperature; the mixed solution was held at this temperature and stirred for 4 h to obtain an initial reaction solution.

Step 2: chlorination: sulfonyl chloride was added dropwise to the initial reaction solution at a rate of $9\times10^{-5}$ mol/[(L ionic liquid)·s], where the temperature was controlled to be 45° C. during the addition of sulfonyl chloride. At the end, totally 6.5 mL of sulfonyl chloride was added to the reaction system. Then, the reaction system was then slowly heated to 65° C. (i.e., the chlorination temperature) over half an hour; the reaction system was then subjected to reflux at this temperature and stirred for 16 h at this temperature to obtain an end-point reaction solution.

Step 3: post-treatment: the end-point reaction solution was hydrolyzed for 10 min to 30 min, and then subjected to suction filtration, washing, drying and other operations to obtain the target product dichloroblue anthrone.

The target product was weighed to be 11.12 g.

Figure 1:
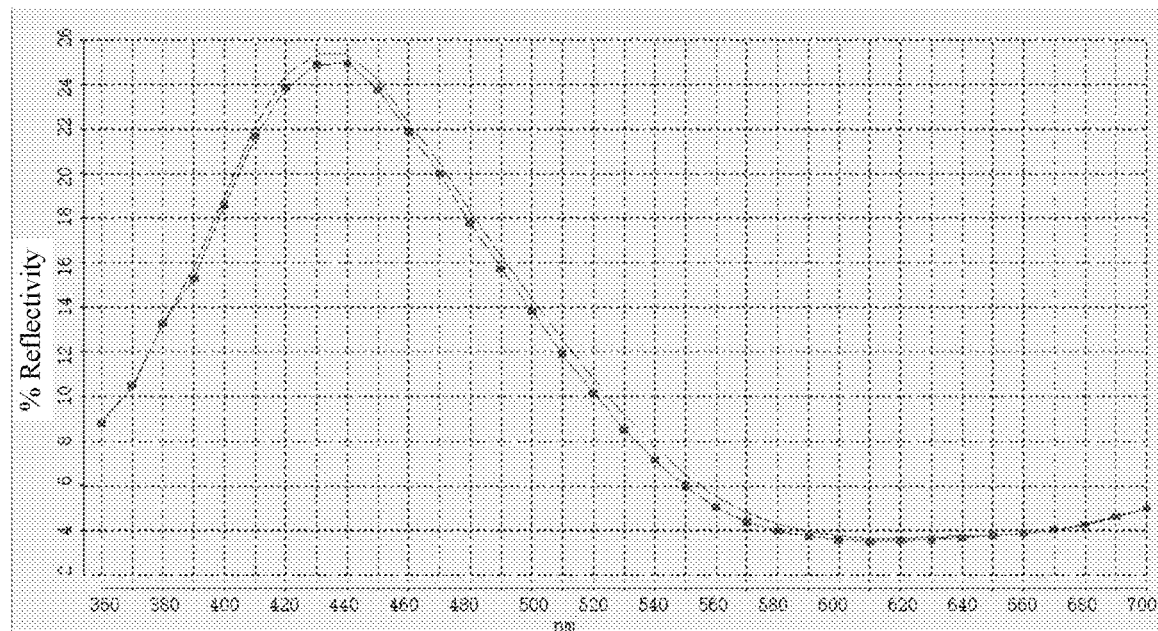
FIG. 1 shows a reflectivity curve diagram of a chlorination product of blue anthrone in Example 1, where a standard control is commodity powder of Vat Blue 6 from Yabang Dyes Company.

Datacolor was used for color measurement, where: commodity powder of Vat Blue 6 from Yabang Dyes Company was used as standard control. The results are shown in FIG. 1. The reflectivity curve of the product obtained in this example is marked with solid dots, and the unmarked ones correspond to the color measurement results of the standard control (similarly hereinafter). The product of this example has a reddish color, and on the basis of not using highly toxic solvents such as nitrobenzene and chlorobenzene, the quality of the product is close to that of the Yabang Dyes Company and has reached the international advanced level.

In this example, the triethylamine hydrochloride-aluminium chloride ionic liquid was used to dissolve blue anthrone, and liquid sulfonyl chloride was used as the chlorinating agent. In the chlorination stage, the entire reaction system was almost liquid and single-phase, the operation was simple, the mass transfer problem caused by the heterogeneous reaction system (for example, using chlorine gas as the chlorinating agent) was avoided in the chlorination process, and the above-mentioned ionic liquid took a catalytic effect on the chlorination process, so there was no need to add additional chlorine for catalysis.

Based on a special anion structure, the ionic liquid with a transition metal halide as the anion showed a certain catalytic effect on the target chlorination reaction. Specifically, in this example, in the hydrochloride triethylamine-aluminium chloride ionic liquid, due to the obvious electron deficiency of Al(III), a certain Lewis acidity and strong reducibility are shown, which can effectively promote the chlorination of blue anthrone in the presence of sulfonyl chloride. In addition, the spatial structure and friction of ions can significantly affect their physical properties such as melting point, adhesion, and density. In production, it is expected that the density and viscosity of the ionic liquid are lower in order to improve the efficiency and solubility of the dissolution. Specifically, in this example, the anion and the cation in the ionic liquid were in strong symmetry in terms of spatial structure, causing weak interaction force; the viscosity of the ionic liquid was low, which is more conducive to dissolution.

Further, in the ionic liquid, the molar ratio of the anion to the cation is controlled to be slightly greater than 2.1:1. Specifically, in this example, the molar ratio of the anion to the cation was 2.15:1, the molar fraction of aluminum chloride was significantly excessive, and a large amount of $[Al_2Cl_7]-$ structures (hereinafter referred to as dimers) were produced in the system, and a small amount of $[Al_3Cl_{10}]-$ structures (hereinafter referred to as trimers) were also produced. By optimizing the anion-to-cation ratio of the ionic liquid, the present disclosure can control the formation ratio of the dimers to the trimers in the obtained ionic liquid, and within the range of the anion-to-cation ratio defined by the present disclosure, the density and viscosity of the ionic liquid are more conducive to the dissolution of the reaction substrate. In this example, using aluminum chloride as the anion, the resulting dimer anion had a larger volume and molecular weight, which increases the mass of substance in unit space. Therefore, under the same conditions, the density of ionic liquid with aluminum chloride as anion is generally high. The volume and molecular weight of the trimer are further greater than those of the dimer, and the greater the molar amount of the generated anion, the smaller the coordination number of the cation; the density of the ionic liquid will further increase, which is not conducive to dissolution. Therefore, in the present disclosure, the design ratio of the anion to the cation should not be greater than 2.5:1 to ensure the dissolution efficiency of the reaction substrate.

In general, the viscosity of ionic liquid is 1 to 3 orders of magnitude larger than that of an organic solvent. High viscosity seriously reduces the diffusion and mass transfer rate of active ions, which is one of the main factors restricting the application of ionic liquid. The viscosity of ionic liquid is mainly affected by van der Waals forces, hydrogen bonds, symmetry of anion and cation, temperature and other factors. Particularly, hydrogen bonds have a greater impact on the viscosity of ionic liquid. In this embodiment, the anion was aluminum chloride. The larger volume of the anion caused charges to be more dispersed; as a result, the interaction between the anion and the cation was reduced, the system had a relatively weak hydrogen bond effect and the viscosity was low. Low viscosity can further enhance the diffusibility and mass transfer ability of ions, which is conducive to the subsequent dissolution.

In addition, the viscosity of the ionic liquid decreases with the increase of temperature. Specifically in the present disclosure, when the temperature rises to 50° C. or above, the decrease of the viscosity becomes more sensitive to the increase of temperature and the magnitude of the decrease increases significantly. As the temperature continues to rise, the decrease trend of viscosity becomes flat. In this embodiment, when the dissolution temperature is 80° C., good dissolution effect of blue anthrone is showed. When the dissolution temperature is designed to be lower than 100° C., existing heat exchange equipment can be used directly to achieve the purpose of maintaining the temperature without using additional equipment (such as heat transfer oil system and more). The dissolution temperature should not be too high, or otherwise the high temperature will destroy the stable structure of the anion in the ionic liquid, which is not conducive to the dissolution of the reaction substrate. High solubility can not only improve the efficiency of the chlorination reaction, but also help reduce the pressure of subsequent solvent recovery.

Further, a slight excess of aluminum chloride can consume water in the system. In the meanwhile, since the raw material used, such as aluminum chloride in this example, is likely to absorb water and gets deliquesced, the synthesis process requires a dry and water-free environment. In addition, the reaction for synthesizing the ionic liquid is an exothermic process. Improper operation will cause the ionic liquid to decompose and change color and introduce impurities. In this case, the ionic liquid has to undergo strict post-treatment before being used. Therefore, during preparation of the ionic liquid, the anion and cation raw materials need to be dried. Moreover, in the present disclosure, adding an excessive amount of anions can also remove water to a certain extent and ensure the quality of the synthesized ionic liquid.

Further, the sulfonyl chloride was slowly added dropwise to the reaction system at a rate not greater than $1.35 \times 10^{-4}$ mol/[(L ionic liquid)·s]. If the sulfonyl chloride is added dropwise at a high rate, part of sulfonyl chloride will be lost under the temperature condition of this reaction system. In addition, the decomposition reaction is exothermic. When the sulfonyl chloride is added dropwise at a relatively high rate for high production efficiency, attention should be paid to controlling the reaction temperature to prevent the reaction from running out of control.

During the research process, it is found by the inventor that when the sulfonyl chloride is added dropwise at a high rate or at a high temperature, it may cause the appearance of smog, and there is an obvious safety hazard. In the case of using a reflux device, although sulfonyl chloride can return to the reaction system again by reflux, ignoring temperature control or control of the addition rate will increase the production burden of the reflux device and increase the production cost.

The chlorinating agent sulfonyl chloride used in the present disclosure has a low boiling point, which is the main reason why the chlorination temperature of the present disclosure is designed to be not higher than the boiling point temperature of the chlorinating agent. However, due to the exothermic property of the chlorination reaction, for the chlorination reaction involved in the present disclosure, in theory, a lower chlorination is preferred (as long as the initiation temperature is higher than the reaction temperature). However, as defined in the present disclosure, room temperature is taken as the starting point of the reaction and no additional refrigeration equipment is used, which can effectively reduce energy consumption and control production costs.

Furthermore, in the reaction of chlorinating blue anthrone, violanthrone and isoviolanthrone, the required degree of chlorination (hereinafter referred to as chlorination level) is mainly controlled by the molar ratio of the chlorinating agent to the reaction substrate, and how long the temperature is held also affects the degree of chlorination. The longer the temperature holding time, the higher the chlorination level.

In other examples, the chlorinating agent in this example was replaced with thionyl chloride and triphosgene, and the other conditions remained unchanged. The blue anthrone was also completely converted (regardless of the case of incomplete dissolution). The actual yield of the obtained target chloride dichloro-blue anthrone also exceeded 90%.

Example 2

Step 0: preparation stage: 0.195 mol of triethylamine hydrochloride and 0.446 mol of aluminum chloride were put in a reaction kettle in sequence, and the resulting solution was then heated to 60° C. and then stirred for 40 min at this temperature to synthesize triethylamine hydrochloride-aluminum chloride ionic liquid.

Step 1: dissolution: 10 g of violanthrone was dissolved into the triethylamine hydrochloride-aluminum chloride ionic liquid, and the resulting solution was heated to 80° C. so that the violanthrone was dissolved at this temperature; the mixed solution was held at this temperature and stirred for 4 h to obtain an initial reaction solution.

Step 2: chlorination: sulfonyl chloride was added dropwise to the initial reaction solution at a rate of $7 \times 10^{-5}$ mol/[(L ionic liquid)·s], where the temperature was controlled to be 60° C. during the addition of sulfonyl chloride. At the end, totally 7.5 mL of sulfonyl chloride was added to the reaction system. Then, the reaction system was then slowly heated to 65° C. (i.e., the chlorination temperature) over half an hour; the reaction system was held at this temperature and stirred for 22 h at this temperature to obtain an end-point reaction solution.

Step 3: post-treatment: the end-point reaction solution was hydrolyzed for 10 min to 30 min, and then subjected to suction filtration, washing, drying and other operations to obtain the target product polychloroviolanthrone.

The target product was weighed to be 13.31 g.

Figure 2:
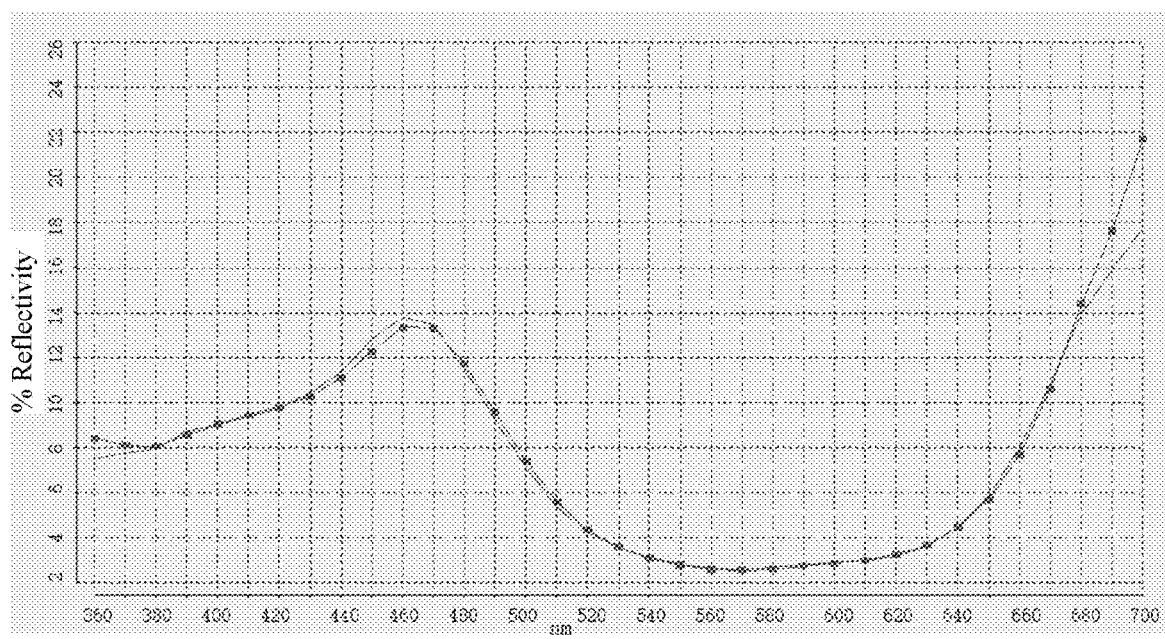
FIG. 2 shows a reflectivity curve of a chlorination product of violanthrone in Example 2, where a standard control is commodity powder of Vat Blue 18 from Atul Company in India.

Datacolor was used for color measurement, where commodity powder of Vat Blue 18 from Atul Company in India was used as the standard control. The results are shown in FIG. 2. The product of this example has a reddish color with watermark, and on the basis of not using highly toxic solvents such as nitrobenzene and chlorobenzene, the product of this example is brighter than that from Atul Company in India.

Example 3

8 mL of sulfonyl chloride was used in this example. The dosage of the reaction solvent in this example was 6/7 of that in Example 2. Other conditions in this example were the same as those in Example 2.

The target product was weighed to be 14.24 g.

Figure 3:
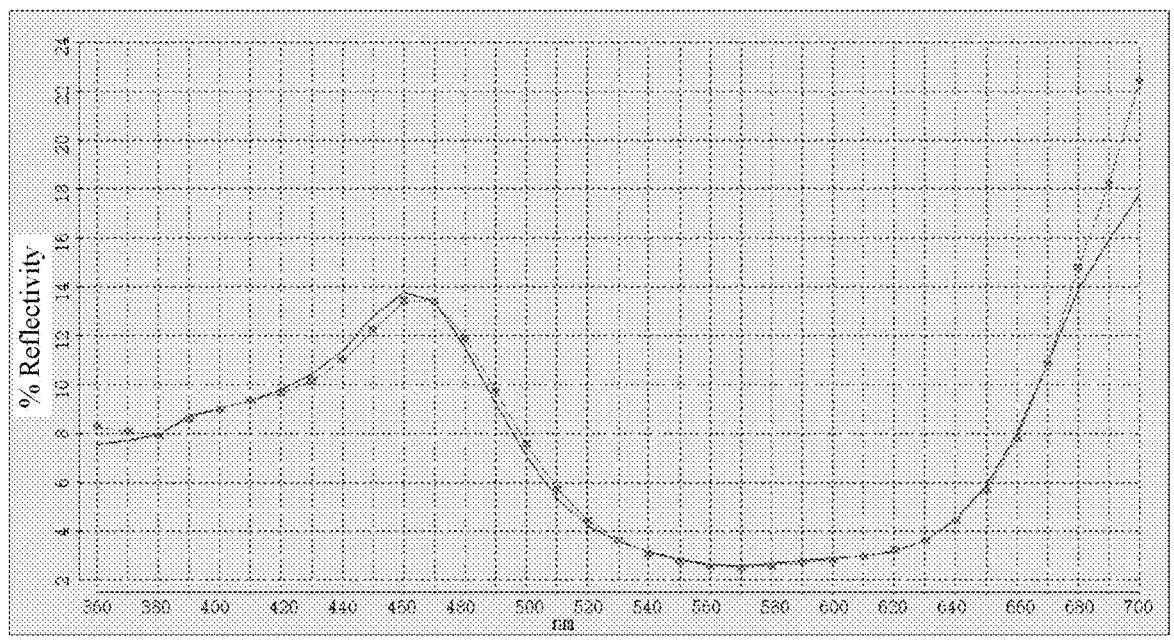
FIG. 3 shows a reflectivity curve of a chlorination product of violanthrone in Example 3, where a standard control is commodity powder of Vat Blue 18 from Atul Company in India.

Datacolor was used for color measurement, where commodity powder of Vat Blue 18 from Atul Company in India was used as the standard control. The results are shown in FIG. 3. The product of this example has a red color with slight watermark.

Example 4

33 mL of sulfonyl chloride was used in this example. The dosage of the reaction solvent in this example was four times that in Example 3. In this example, the mass of the reaction substrate was 30.17 g, sulfonyl chloride was added dropwise at a rate of $1.35 \times 10^{-4}$ mol/[(L ionic liquid)·s] at a temperature of 46° C., and the reaction solution was held at this temperature and stirred for 20 h. Other conditions in this example were the same as those in Example 3.

The target product was weighed to be 44.72 g.

Figure 4:
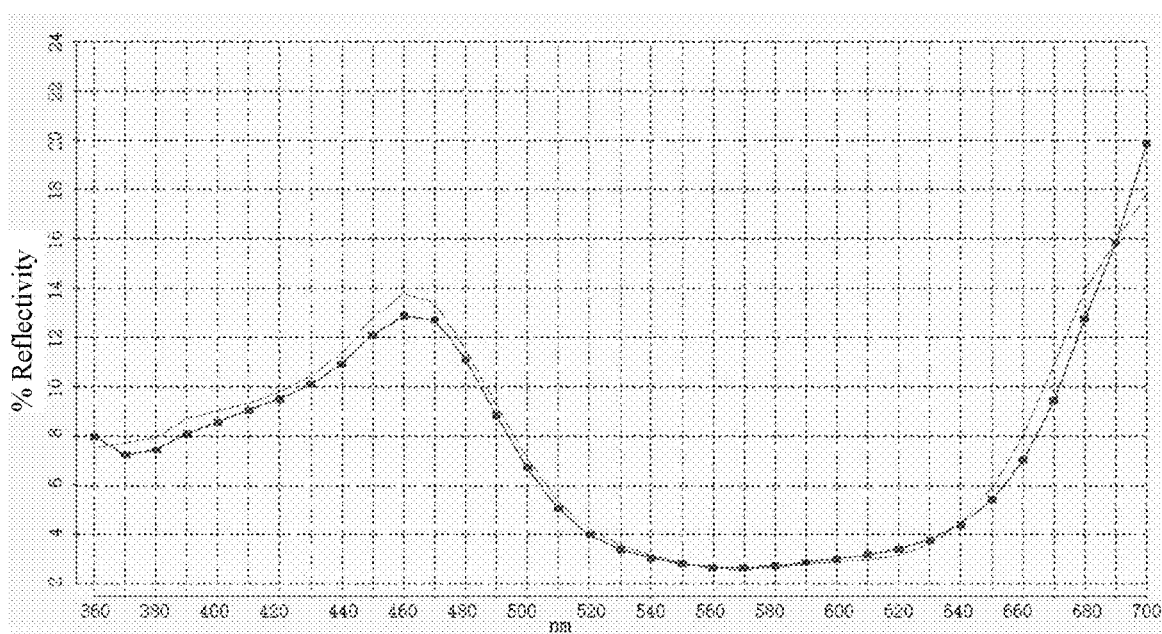
FIG. 4 shows a reflectivity curve of a chlorination product of violanthrone in Example 4, where a standard control is commodity powder of Vat Blue 18 from Atul Company in India.
Figure 5:
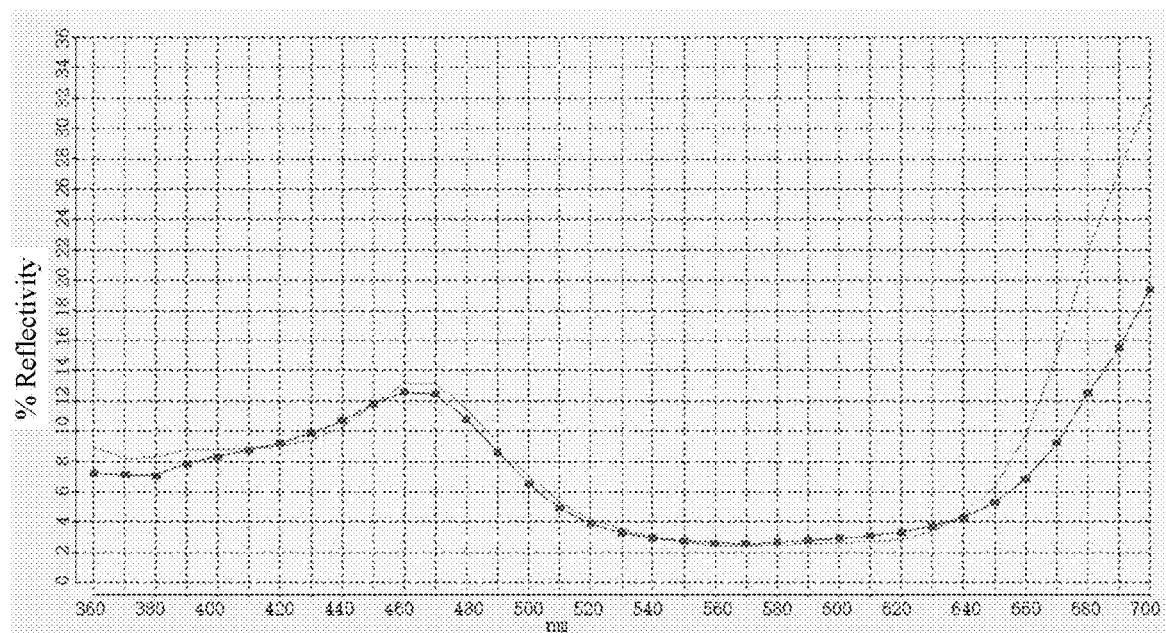
FIG. 5 shows a reflectivity curve of a chlorination product of violanthrone in Example 4, where a standard control is commodity powder of Vat Blue 22 from Atul Company in India.

Datacolor was used for color measurement, where commodity powder of Vat Blue 18 from Atul Company in India was used as the standard control, and the results are shown in FIG. 4; commodity powder of Vat Blue 22 from Atul Company in India was used as the standard control, and the results are shown in FIG. 4. The product of this example has a reddish color with slight watermark.

In this case, comparing the experimental results of Examples 2, 3, and 4, it can be seen that the product obtained in Example 2 is closer to the commodity powder of Vat Blue 18 from Atul Company in India, the product obtained in Example 4 is closer to the commodity powder of Vat Blue 22, the quality of the product in Example 3 is between the quality of the commodity powder of Vat Blue 18 and the quality of the commodity powder of Vat Blue 22, and this is caused by the difference in actual chlorine level. Therefore, in actual production, the process can be selected in the technical solution described by the present invention according to the needs based on different chlorination requirements to achieve controllable chlorination, in order to better meet the market demand.

Example 5

In this example, triethylamine hydrochloride-aluminum chloride ionic liquid was used as a reaction solvent, in which 0.384 mol of aluminum chloride and 0.167 mol of triethylamine hydrochloride were added. Other conditions in this example were the same as those in Example 2.

Example 6

In this example, triethylamine hydrochloride-aluminum chloride ionic liquid was used as a reaction solvent, in which 0.344 mol of aluminum chloride and 0.137 mol of triethylamine hydrochloride were added, and the temperature was controlled to be 45° C. during the addition of sulfonyl chloride. At the end of the addition, totally 6.5 mL of sulfonyl chloride was added to the reaction system. Other conditions in this example were the same as those in Example 2.

Example 7

In this example, the reaction time was controlled to be 40 h. Other conditions in this example were the same as those in Example 2, and the degree of chlorination was deepened.

Example 8

In this example, the chlorination system was pressurized to 4 atm (gauge pressure), and the reaction time was controlled to be 2 h. Other conditions in this example were the same as those in Example 2.

In other examples, the chlorination system was pressurized to 3 atm or 2 atm, and the reaction time can be shortened correspondingly compared with that in Example 2.

Example 9

In this example, the method for chlorinating violanthrone as disclosed in the present disclosure was put into scale-up production.

Step 0: preparation stage: 767 kg of triethylamine hydrochloride and 900 kg of aluminum chloride were put in a reaction kettle in sequence, and the resulting solution was then stirred for 45 min; another 600 kg of aluminum chloride was then added while stirring was stopped, and the resulting solution was then stirred for 45 min; another 300 kg of aluminum chloride was added while stirring was stopped, and the resulting solution was then stirred for 30 min during which the temperature was maintained not lower than 60° C., to synthesize triethylamine hydrochloride-aluminum chloride ionic liquid.

Step 1: dissolution: 250 kg of violanthrone was dissolved into the triethylamine hydrochloride-aluminum chloride ionic liquid, and the resulting solution was heated to 80° C. so that the violanthrone was dissolved at this temperature; the mixed solution was held at this temperature and stirred for 6 h to obtain an initial reaction solution.

Step 2: chlorination: sulfonyl chloride was added dropwise to the initial reaction solution at a rate of $1.35 \times 10^{-4}$ mol/[(L ionic liquid)·s], where the temperature was controlled to be not higher than 60° C. during the addition of sulfonyl chloride. At the end, totally 200 L of sulfonyl chloride was added to the reaction system. Then, the reaction system was then slowly heated to 65° C. (i.e., the chlorination temperature) over half an hour; the reaction system was then held at this temperature and stirred for 20 h at this temperature to obtain an end-point reaction solution.

Step 3: post-treatment: the end-point reaction solution was hydrolyzed for 30 min, and then subjected to suction filtration, washing, drying and other operations to obtain the target product polychloroviolanthrone.

Example 10

Step 0: preparation stage: 0.137 mol of triethylamine hydrochloride and 0.344 mol of aluminum chloride were put in a reaction kettle in sequence, and the resulting solution was then heated to 60° C. and then stirred for 40 min at this temperature to synthesize triethylamine hydrochloride-aluminum chloride ionic liquid.

Step 1: dissolution: 10 g of isoviolanthrone was dissolved into the triethylamine hydrochloride-aluminum chloride ionic liquid, and the resulting solution was heated to 80° C. so that the violanthrone was dissolved at this temperature; the mixed solution was held at this temperature and stirred for 4 h to obtain an initial reaction solution.

Step 2: chlorination: sulfonyl chloride was added dropwise to the initial reaction solution at a rate of $6 \times 10^{-5}$ mol/[(L ionic liquid)·s], where the temperature was controlled to be 45° C. during the addition of sulfonyl chloride. At the end, totally 3.9 mL of sulfonyl chloride was added to the reaction system. Then, the reaction system was then slowly heated to 65° C. (i.e., the chlorination temperature) over half an hour; the reaction system was held at this temperature and stirred for 24 h at this temperature to obtain an end-point reaction solution.

Step 3: post-treatment: the end-point reaction solution was hydrolyzed for 10 min to 30 min, and then subjected to suction filtration, washing, drying and other operations to obtain the target product dichloroisoviolanthrone.

The target product was weighed to be 11 g.

Figure 6:
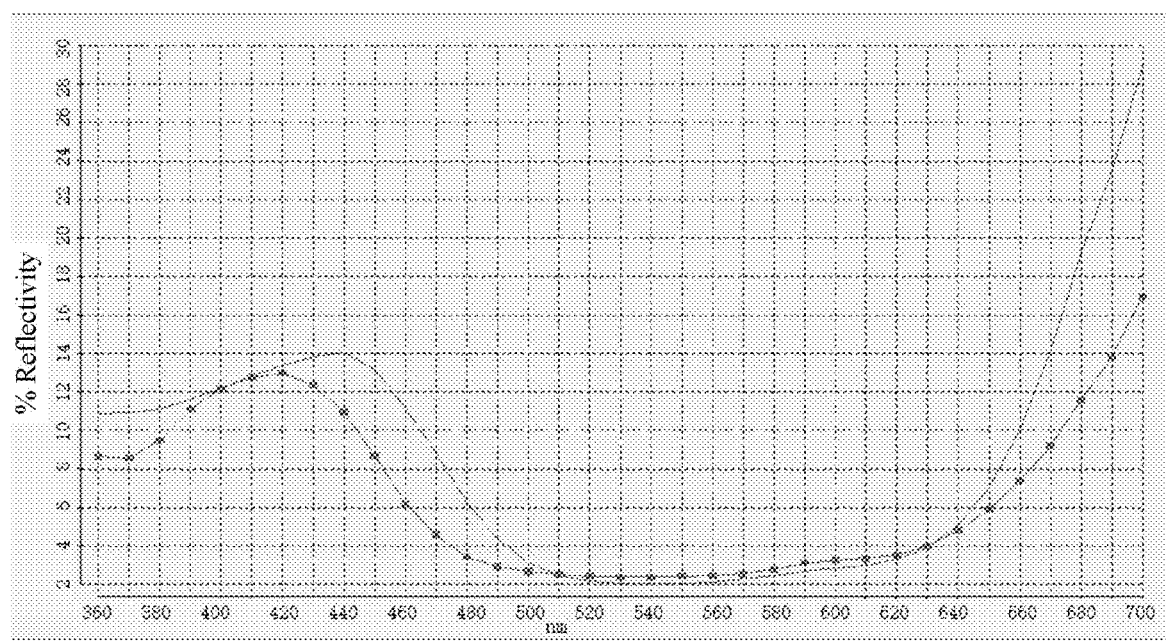
FIG. 6 shows a reflectivity curve of a chlorination product of isoviolanthrone in Example 10, where a standard control is commodity powder of Vat Violet 1 from Chongqing Huacai Company.

Datacolor was used for color measurement, where commodity powder of Vat Violet 1 from Chongqing Huacai Company was used as the standard control. The results are shown in FIG. 6. The product of this example has a light and bluish color.

Example 11

In this example, 7.5 mL of sulfonyl chloride was used, the dosage of the reaction solvent was twice that in Example 8, the mass of the reaction substrate was 19.09 g, sulfonyl chloride was added dropwise at a rate of $4 \times 10^{-5}$ mol/[(L ionic liquid)·s], and other conditions were the same as in Example 8.

The target product was weighed to be 22.85 g.

Figure 7:
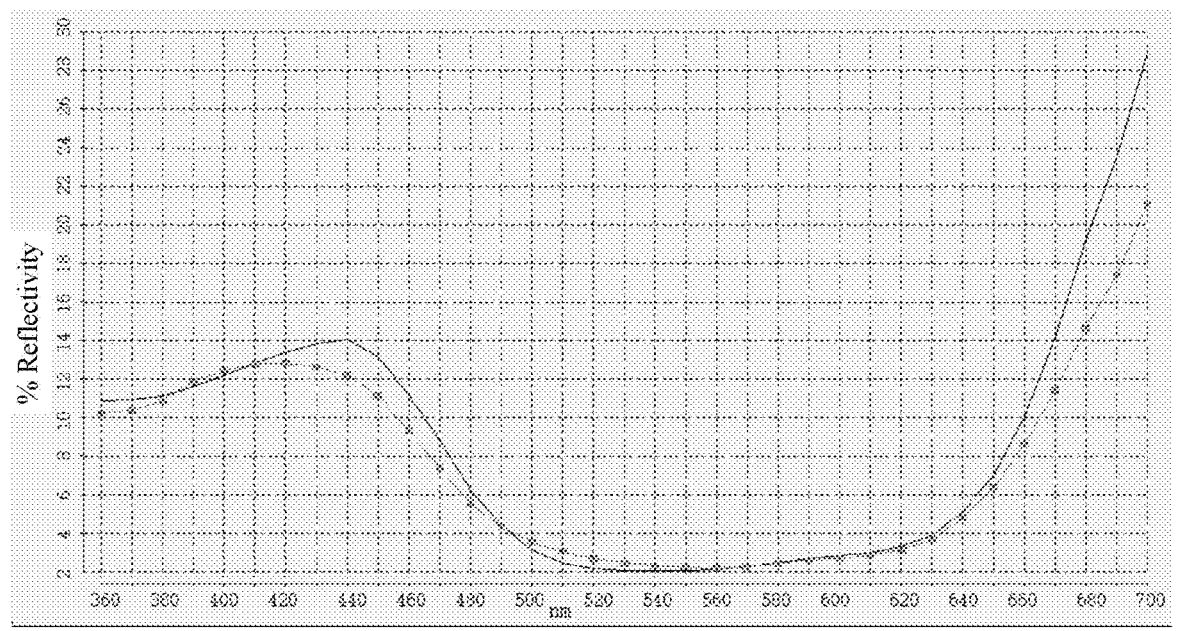
FIG. 7 shows a reflectivity curve of a chlorination product of isoviolanthrone in Example 11, where a standard control is commodity powder of Vat Violet 1 from Chongqing Huacai Company.

Datacolor was used for color measurement, where commodity powder of Vat Violet 1 from Chongqing Huacai Company was used as the standard control. The results are shown in FIG. 7. The product of this example has a slightly light and reddish color.

Example 12

Step 0: preparation stage: 0.381 mol of triethylamine hydrochloride and 0.839 mol of aluminum chloride were put in a reaction kettle in sequence, and the resulting solution was then heated to 60° C. and then stirred for 40 min at this temperature to synthesize triethylamine hydrochloride-aluminum chloride ionic liquid.

Step 1: dissolution: 15 g of isoviolanthrone was dissolved into the triethylamine hydrochloride-aluminum chloride ionic liquid, and the resulting solution was heated to 80° C. so that the violanthrone was dissolved at this temperature; the mixed solution was held at this temperature and stirred for 6 h to obtain an initial reaction solution.

Step 2: chlorination: sulfonyl chloride was added dropwise to the initial reaction solution at a rate of $6 \times 10^{-5}$ mol/[(L ionic liquid)·s], where the temperature was controlled to be 45° C. during the addition of sulfonyl chloride. At the end, totally 5.0 mL of sulfonyl chloride was added to the reaction system. Then, the reaction system was then slowly heated to 65° C. (i.e., the chlorination temperature) over half an hour; the reaction system was then held at this temperature and stirred for 10 h to 25 h at this temperature to obtain an end-point reaction solution.

Step 3: post-treatment: the end-point reaction solution was hydrolyzed for 10 min to 30 min, and then subjected to suction filtration, washing, drying and other operations to obtain the target product dichloroisoviolanthrone.

The target product was weighed and subjected to Datacolor for color measurement.

Comparing this example with Example 10, it can be seen that the dissolution speed and effect can also be achieved by controlling the mass ratio between the ionic liquid and the reaction substrate. When the mass of the reaction substrate is increased to 15 g, the mass of the solvent (i.e., the mass of the ionic liquid) also increased accordingly), but in this case the dissolution time is extended from 4 h to 6 h and the dissolution effect of this example is the same as that of Example 10. In the samples taken from the bottom of the reactor, no large particles are found.

In another example, on the basis of this example, the dissolution time is extended to 8 h, which is not significantly different from 6 h.

Example 13

In this example, triethylamine hydrochloride-aluminum chloride ionic liquid was used as a reaction solvent and totally 5.3 mL of sulfony chloride was added in this reaction system. Other conditions in this example were the same as those in Example 12.

Example 14

In this example, triethylamine hydrochloride-aluminum chloride ionic liquid was used as a reaction solvent and totally 5.6 mL of sulfony chloride was added in this reaction system. Other conditions in this example were the same as those in Example 12.

Example 15

In this example, triethylamine hydrochloride-aluminum chloride ionic liquid was used as a reaction solvent; isoviolanthrone was dissolved in the triethylamine hydrochloride-aluminum chloride ionic liquid for 8 h and totally 5.6 mL of sulfony chloride was added in this reaction system. Other conditions in this example were the same as those in Example 12.

According to the above experimental data results, in the examples of the present disclosure, there is a phenomenon that the mass of the actually harvested product exceeds the mass of the theoretically harvestable chlorination product, for the reason that, after a long time of reaction, the target product obtained is mixed with products with an unexpected chlorination level. For example, after isoviolanthrone is subjected to the above chlorination, in addition to dichloroisoviolanthrone, the obtained product may also include trichloroisoviolanthrone, tetrachloroisoviolanthrone and even chlorination products with a higher chlorination level. As mentioned above, the chlorination level is mainly related to the dosage of sulfonyl chloride added dropwise and the temperature holding time. However, sometimes, in actual production, a little higher chlorination level may also be accepted, which can increase the depth and brightness of the color. In the actual use of dyes, a variety of original dyes are often compounded into a desired color, which is then used in printing and dyeing. In addition, in the actual chlorination reaction, it is difficult to accurately control the chlorination level. Therefore, in the present disclosure, the final chlorination product is often a mixture, and too high chlorination level results in slightly more products actually harvested.

In theory, in the chlorination process of the present disclosure, after 2 to 40 h of temperature holding, the reaction substrate has been completely reacted, but due to incomplete dissolution, the actual conversion rate of the reaction substrate was between 95% and 100%.

In this way, the longer the temperature holding time, the higher the chlorination level. However, in order to facilitate the operation in production, during the process design of the present disclosure, the chlorination level is mainly controlled by controlling the molar ratio of the reaction substrate to the chlorinating agent and the reaction time is designed in a unified manner; therefore, the complexity of the operation of the workers is reduced and the average quality of the product is improved.

In another example, through investigating the chlorination effects over 8 h, 12 h, 16 h, 20 h, 22 h, and 25 h of temperature holding time, it is found that when the temperature holding time is shorter than 16 h, for example, when the temperature holding time is 12 h, there is a certain difference between the product mass obtained and the desired product mass, but this difference is within an effective range; when the temperature holding time is more than 16 h, the difference in product mass is not great. On this basis, the chlorination system is pressurized to shorten the temperature holding time.

In addition, in the step of stirring with the temperature held, especially in industrial mass production, it is required to pay special attention to temperature control to prevent partial temperature flying during the reaction. Otherwise, in a worse case, it will be difficult to control the chlorination level, which will affect the mass of the product, and in the worst case, the reaction will be out of control and cause safety accidents.

In another example, triethylamine hydrochloride-aluminum chloride ionic liquid was used as the reaction solvent, in which the anion was replaced with ferric chloride. Other conditions in this example were the same as those in Examples 1, 2 and 14, and then the chlorination process as described above was also achieved. Correspondingly, the anion can also be replaced with other transition metal halides, all of which can effectively chlorinate blue anthrone, violanthrone and isoflavanthrone to obtain the target chlorination products.

In another example, N-ethylpyridine-aluminum chloride ionic liquid is used as the reaction solvent, in which the cation was replaced with N-ethylpyridine. Other conditions in this example were the same as those in Examples 1, 2 and 14, and then the chlorination process as described above was also achieved. Correspondingly, the cation can also be replaced with dimethylaniline hydrochloride, urea, triethylamine sulfate, dimethylaniline sulfate, and more, and the anion can be replaced with a transition metal halide such as aluminum chloride, ferric chloride, and more. The solutions can both effectively chlorinate blue anthrone, violanthrone and isoviolanthrone to obtain the target chlorinated products.

In addition to the above-mentioned preferred embodiments, the present disclosure has other embodiments. Those skilled in the art can make various changes and modifications according to the present disclosure. As long as these changes and modifications do not depart from the spirit of the present disclosure, they should all fall within the scope defined in the claims of the present disclosure.

What is claimed is:

1. A method for chlorinating blue anthrone, violanthrone or isoviolanthrone, comprising:
    causing a reaction substrate which is any one of blue anthrone, violanthrone and isoviolanthrone to react with a chlorinating agent which is any one of sulfonyl chloride, thionyl chloride and triphosgene in a reaction solvent which is a Lewis acid ionic liquid for 2 h to 40 h at a chlorination temperature not lower than a room temperature and not higher than a boiling point of the chlorinating agent,
    wherein anions in the Lewis acid ionic liquid are of a transition metal halide.

2. The method for chlorinating blue anthrone, violanthrone or isoviolanthrone according to claim 1, wherein
    the anions in the Lewis acid ionic liquid are of any one of aluminum chloride and ferric chloride.

3. The method for chlorinating blue anthrone, violanthrone or isoviolanthrone according to claim 2, wherein
    specific chlorination steps are as follows:
    step 1: dissolution: dissolving the reaction substrate in the Lewis acid ionic liquid at a dissolution temperature of 30° C. to 150° C., holding the dissolution temperature and stirring for not less than 3 h to obtain an initial reaction solution;
    step 2: chlorination: adding the chlorinating agent dropwise to the initial reaction solution, wherein a temperature of the initial reaction solution is controlled to be not higher than 60° C. during addition of the chlorinating agent; and then holding the chlorination temperature and stirring for 2 h to 40 h to obtain an end-point reaction solution; and
    step 3: post-treatment: hydrolyzing the end-point reaction solution for 10 min to 30 min, and then carrying out suction filtration, washing, and drying to obtain a target chlorination product.

4. The method for chlorinating blue anthrone, violanthrone or isoviolanthrone according to claim 2, wherein
    a molar ratio of the anion to cation in the Lewis acid ionic liquid is (2.0 to 2.7):1.

5. The method for chlorinating blue anthrone, violanthrone or isoviolanthrone according to claim 4, wherein
    specific chlorination steps are as follows:
    step 1: dissolution: dissolving the reaction substrate in the Lewis acid ionic liquid at a dissolution temperature of 30° C. to 150° C., holding the dissolution temperature and stirring for not less than 3 h to obtain an initial reaction solution;
    step 2: chlorination: adding the chlorinating agent dropwise to the initial reaction solution, wherein a temperature of the initial reaction solution is controlled to be not higher than 60° C. during addition of the chlorinating agent; and then holding the chlorination temperature and stirring for 2 h to 40 h to obtain an end-point reaction solution; and
    step 3: post-treatment: hydrolyzing the end-point reaction solution for 10 min to 30 min, and then carrying out suction filtration, washing, and drying to obtain a target chlorination product.

6. The method for chlorinating blue anthrone, violanthrone or isoviolanthrone according to claim 4, wherein
    the cations in the Lewis acid ionic liquid are of any one of a tertiary amine hydrochloride, a tertiary amine sulfate, N-alkylpyridine, and urea.

7. The method for chlorinating blue anthrone, violanthrone or isoviolanthrone according to claim 6, wherein
    specific chlorination steps are as follows:
    step 1: dissolution: dissolving the reaction substrate in the Lewis acid ionic liquid at a dissolution temperature of 30° C. to 150° C., holding the dissolution temperature and stirring for not less than 3 h to obtain an initial reaction solution;
    step 2: chlorination: adding the chlorinating agent dropwise to the initial reaction solution, wherein a temperature of the initial reaction solution is controlled to be not higher than 60° C. during addition of the chlorinating agent; and then holding the chlorination temperature and stirring for 2 h to 40 h to obtain an end-point reaction solution; and
    step 3: post-treatment: hydrolyzing the end-point reaction solution for 10 min to 30 min, and then carrying out suction filtration, washing, and drying to obtain a target chlorination product.

8. The method for chlorinating blue anthrone, violanthrone or isoviolanthrone according to claim 1, wherein
    a mass concentration of the reaction substrate in the Lewis acid ionic liquid is 0.08 g/mL to 0.5 g/mL.

9. The method for chlorinating blue anthrone, violanthrone or isoviolanthrone according to claim 8, wherein
    specific chlorination steps are as follows:
    step 1: dissolution: dissolving the reaction substrate in the Lewis acid ionic liquid at a dissolution temperature of 30° C. to 150° C., holding the dissolution temperature and stirring for not less than 3 h to obtain an initial reaction solution;
    step 2: chlorination: adding the chlorinating agent dropwise to the initial reaction solution, wherein a temperature of the initial reaction solution is controlled to be not higher than 60° C. during addition of the chlorinating agent; and then holding the chlorination temperature and stirring for 2 h to 40 h to obtain an end-point reaction solution; and
    step 3: post-treatment: hydrolyzing the end-point reaction solution for 10 min to 30 min, and then carrying out suction filtration, washing, and drying to obtain a target chlorination product.

10. The method for chlorinating blue anthrone, violanthrone or isoviolanthrone according to claim 1, wherein
    for linking every 1 mole of chlorine atom to the reaction substrate, 0.3 mole to 6 mole of the chlorinating agent is added.

11. The method for chlorinating blue anthrone, violanthrone or isoviolanthrone according to claim 10, wherein
    specific chlorination steps are as follows:
    step 1: dissolution: dissolving the reaction substrate in the Lewis acid ionic liquid at a dissolution temperature of 30° C. to 150° C., holding the dissolution temperature and stirring for not less than 3 h to obtain an initial reaction solution;
    step 2: chlorination: adding the chlorinating agent dropwise to the initial reaction solution, wherein a temperature of the initial reaction solution is controlled to be not higher than 60° C. during addition of the chlorinating agent; and then holding the chlorination temperature and stirring for 2 h to 40 h to obtain an end-point reaction solution; and step 3: post-treatment: hydrolyzing the end-point reaction solution for 10 min to 30 min, and then carrying out suction filtration, washing, and drying to obtain a target chlorination product.

12. The method for chlorinating blue anthrone, violanthrone or isoviolanthrone according to claim 1, wherein specific chlorination steps are as follows:

step 1: dissolution: dissolving the reaction substrate in the Lewis acid ionic liquid at a dissolution temperature of 30° C. to 150° C., holding the dissolution temperature and stirring for not less than 3 h to obtain an initial reaction solution;

step 2: chlorination: adding the chlorinating agent dropwise to the initial reaction solution, wherein a temperature of the initial reaction solution is controlled to be not higher than 60° C. during addition of the chlorinating agent; and then holding the chlorination temperature and stirring for 2 h to 40 h to obtain an end-point reaction solution; and step 3: post-treatment: hydrolyzing the end-point reaction solution for 10 min to 30 min, and then carrying out suction filtration, washing, and drying to obtain a target chlorination product.

13. The method for chlorinating blue anthrone, violanthrone or isoviolanthrone according to claim 12, wherein the chlorinating agent is added dropwise at a rate not greater than $1.35 \times 10^{-4}$ mol/[(L ionic liquid)·s].

14. The method for chlorinating blue anthrone, violanthrone or isoviolanthrone according to claim 13, wherein when the chlorinating agent is added dropwise, the temperature of the initial reaction liquid is controlled to be 20° C. to 60° C.

15. The method for chlorinating blue anthrone, violanthrone or isoviolanthrone according to claim 14, wherein when the reaction substrate is blue anthrone, the target chlorination product is dichloro-blue anthrone;

when the reaction substrate is violanthrone, the target chlorination product is polychloroviolanthrone;

when the reaction substrate is isoviolanthrone, the target chlorination product is dichloroisoviolanthrone.

* * * * *